United States Patent [19]

LaMattina

[11] Patent Number: 4,636,498
[45] Date of Patent: * Jan. 13, 1987

[54] FORMULATION OF ANTIINFLAMMATORY DRUGS

[75] Inventor: John L. LaMattina, Ledyard, Conn.

[73] Assignee: Pfizer Inc., New York, N.Y.

[*] Notice: The portion of the term of this patent subsequent to Jan. 28, 2003 has been disclaimed.

[21] Appl. No.: 765,415

[22] Filed: Aug. 15, 1985

Related U.S. Application Data

[63] Continuation-in-part of Ser. No. 659,752, Oct. 11, 1984, abandoned.

[51] Int. Cl.[4] .................... A61K 31/54; A61K 31/425
[52] U.S. Cl. ..................................... 514/222; 514/371
[58] Field of Search ................ 514/225, 371, 367, 222

[56] References Cited

U.S. PATENT DOCUMENTS 4,230,717 10/1980 Lovelace ............................. 424/274
4,447,443 5/1984 Goldenberg .................... 424/273 R

FOREIGN PATENT DOCUMENTS 2105193 3/1983 United Kingdom .
2105588 3/1983 United Kingdom .

OTHER PUBLICATIONS

Okabe et al., Am. J. Dig. Dis 22, pp. 677-684 (1977).
Brown et al., Eur. J. Pharmacol. 51, pp. 275-283 (1978).
Hayden et al., J. Pharm. Pharmacol. 30, pp. 244-246 (1977).
Djahanguiri et al., Eur. J. Pharmacol. 51, pp. 77-79 (1978).
Takeda et al., Arzneim-Forsch 32, pp. 734-737 (1982).
Croker et al., Ann. Rheum. Dis. 39, pp. 275-278 (1980).

Primary Examiner—Stanley J. Friedman
Attorney, Agent, or Firm—Charles J. Knuth; Albert E. Frost; Robert K. Blackwood

[57] ABSTRACT

An improved antiinflammatory composition and method of treating inflammation which employs a combination of an antiinflammatory agent (e.g. indomethacin or an oxicam) with a histamine-$H_2$ antagonist selected from the group consisting of 2-guanidino-4-(4-imidazolyl)thiazole, 2-guanidino-4-(2-methyl-4-imidazolyl)thiazole, 2-(N-benzyl-N'-guanidino)-4-(2-methyl-4-imidazolyl)thiazole, 2-(N-pentyl-N'-guanidino)-4-(2-methyl-4-imidazolyl)thiazole and 2-guanidino-4-[2-(hexylamino)-4-imidazolyl]thiazole.

20 Claims, No Drawings

FORMULATION OF ANTIINFLAMMATORY DRUGS

CROSS REFERENCE TO RELATED APPLICATION

This application is a continuation-in-part of copending U.S. application, Ser. No. 659,752, filed Oct. 11, 1984, now abandoned.

BACKGROUND OF THE INVENTION

The present invention is concerned with an improved antiinflammatory composition and method of treating inflammation which employs a nonsteroidal antiinflammatory agent (e.g. indomethacin or an oxicam such as piroxicam, sudoxicam, tenoxicam, isoxicam; the generic names used here and elsewhere herein are from the USAN and the USP Dictionary of Drug Names, 1961–1981, Griffiths et al., ed., U.S. Pharmacopeial Convention Inc., Rockville, Md., 1984) in combination with a histamine-$H_2$-antagonist selected from the group consisting of 2-guanidino-4-(4-imidazolyl)thiazole, 2-guanidino-4-(2-methyl-4-imidazolyl)thiazole, 2-(N-benzyl-N'-guanidino)-4-(2-methyl-4-imidazolyl)thiazole, 2-(N-pentyl-N'-guanidino)-4-(2-methyl-4-imidazolyl)thiazole and 2-guanidino-4-[2-(hexylamino)-4-imidazolyl]thiazole.

Gastrointestinal irritation, sometimes culminating in ulcers, is a side effect commonly associated, to one degree or another, with nonsteroidal antiinflammatory agents. (For an essentially complete summary of known nonsteroidal antiinflammatory agents, see Goldenberg, U.S. Pat. No. 4,447,443.) In many cases, individuals requiring such antiinflammatory treatment are precluded from enjoying the benefits thereof because of their susceptibility to such irritation or ulcers. The present combination of antiinflammatory agents with $H_2$-antagonist agents (which are gastric acid antisecretory agents, or gastric acid antisecretory agents and show cytoprotective activity as well) permits desirable antiinflammatory therapy while preventing or ameliorating said gastrointestinal irritation and ulcers. In addition, in certain cases, there is an enhancement of the beneficial effect in the treatment of rheumatoid arthritis with the present combination.

Other histamine-$H_2$-antagonist (gastric secretory inhibitory) compounds such as ranitidine, cimetidine and 1-methyl-5-[[3-[3-(1-piperidinylmethyl)phenoxy]propylamino]]-1H-1,2,4-triazole-3-methanol, have been previously combined with indomethacin, piroxicam and other antiinflammatory agents for this purpose. See for example U.K. Patent Applications Nos. 2,105,193 and 2,105,588; and Lovelace, U.S. Pat. No. 4,230,717. More recently, the histidine decarboxylase inhibitor, alpha-fluoromethylhistidine of Kollonitsch et al., U.S. Pat. No. 4,325,961, has been reported to provide synergistic antiinflammatory activity, particularly with indomethacin, Goldenberg, U.S. Pat. No. 4,447,443. The ulcerogenicity of this combination is not discussed.

The use of 2-guanidino-4-(2-methyl-4-imidazolyl)thiazole per se in the treatment of rheumatoid arthritis is the subject of U.S. patent application, Ser. No. 659,750 by Larson, filed on Oct. 11, 1984, concurrently with the parent of the present application. Improved antiinflammatory salts of piroxicam, including a salt with 2-guanidino-4-(2-methyl-4-imidazolyl)thiazole, are the subject of U.S. patent application Ser. No. 659,733 by Lombardino, also filed on Oct. 11, 1984.

The antiinflammatory agents employed in the present invention are known. For example The Merck Index, 10th Ed., 1983 contains, among others, monographs concerning indomethacin (No. 4852), isoxicam (No. 5085), piroxicam (No. 7378) and tenoxicam (No. 8980). Preparation of the oxicams and their utility as antiinflammatory agents are further disclosed in U.S. Pat. Nos. 3,591,584; 3,787,324; 3,822,258; 3,892,740; and 4,434,164.

The histamine-$H_2$-antagonists of the present invention are also known (see U.S. Pat. Nos. 4,435,396 and 4,374,843), or, in the cases of 2-(N-benzyl-N'-guanidino)-4-(2-methyl-4-imidazolyl)thiazole and 2-(N-pentyl-N'-guanidino)-4-(2-methyl-4-imidazolyl)thiazole, are the subject of copending U.S. application Ser. No. 605,510, of Reiter filed Apr. 30, 1984, for "2-(N-Substituted guanidino)-4-heteroarylthiazole Antiulcer Agents." The method of preparing said N-benzyl and N-pentyl guanidino compounds and employing same as an antiulcer and/or as a gastric antisecretory agent is also detailed hereinafter. Also detailed hereinafter, but not here claimed, is an improved method of preparing 2-guanidino-4-(2-methyl-4-imidazolyl)thiazole and certain of its salts.

SUMMARY OF THE INVENTION

The present invention particularly concerns an improved antiinflammatory composition which comprises an antiinflammatory amount of indomethacin or an oxicam, or a pharmaceutically-acceptable salt thereof, in combination with a gastric anti-irritation and ulcer-inhibiting amount of a compound selected from the group consisting of 2-guanidino-4-(4-imidazolyl)thiazole, 2-guanidino-4-(2-methyl-4-imidazolyl)thiazole, 2-(N-benzyl-N'-guanidino)-4-(2-methyl-4-imidazolyl)thiazole, 2-(N-pentyl-N'-guanidino-4-(2-methyl-4-imidazolyl)thiazole, 2-guanidino-4-[2-(hexylamino)-4-imidazolyl]thiazole, and the pharmaceutically-acceptable salts thereof.

The present invention is also concerned with an improved method for the treatment of inflammation which comprises, in addition to treatment with an antiinflammatory amount of said antiinflammatory compound, treatment with a gastric anti-irritation and ulcer-inhibiting amount of one of said thiazole compounds.

The oxicams employed in the present invention are of the formula

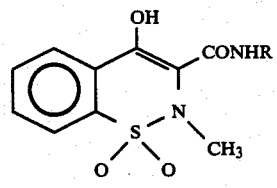

(I)

or

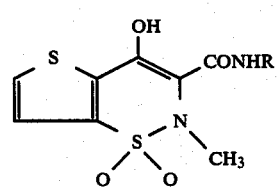

(II)

wherein R is

-continued

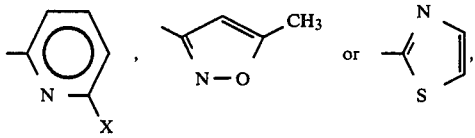

and X is hydrogen, chloro or methyl; or a pharmaceutically acceptable salt thereof.

Preferred antiinflammatory agents in the present invention are tenoxicam (of the formula II wherein R is 2-pyridyl), isoxicam (of the formula I wherein R is 5-methyl-3-isoxazolyl), sudoxicam (of the formula I wherein R is 2-thiazolyl), more particularly, piroxicam (of the formula I wherein R is 2-pyridyl), and most particularly, the ethanolamine salt of piroxicam.

DETAILED DESCRIPTION OF THE INVENTION

The clinical value of the present improved formulation of antiinflammatory agents is reflected by appropriate animal studies. Typical experimental protocols for determining the ability of one or another of the present gastric secretory inhibiting compounds to prevent or reduce gastric lesioning induced by an antiinflammatory agent are illustrated in specific examples below.

The further clinical value of certain of the present improved formulations in the treatment of rheumatoid arthritis is reflected by animal studies (also specifically illustrated in the Examples below) in which the efficacy of the antiinflammatory compound against adjuvant arthritis is significantly enhanced by the co-administration of one of the present antisecretory or antisecretory/cytoprotective compounds.

The present invention is readily carried out. The antiinflammatory agent and the antiulcer agent may be dosed separately, each according to dosage regimens (amounts, frequency, routes and compositions) as specified in the prior art, for example, in references cited above or further cited in said references, or, in the cases of 2-(N-benzyl-N'-guanidino)-4-(2-methyl-4-imidazolyl)thiazole and 2-(N-pentyl-N'-guanidino)-4-(2-methyl-4-imidazolyl)thiazole as detailed in the paragraphs which follow.

The antiulcer utility of the latter two compounds in mammals, including man, is reflected in their antisecretory (histamine-$H_2$-antagonism) and their inhibition of ethanol-induced ulcers in rats, as detailed in the Examples below. To inhibit (prevent or treat) gastric ulcers in a mammalian subject, this compound is administered by a variety of conventional routes of administration including orally and parenterally. Preferably, the compound is administered orally. In general, it will be administered orally at doses between about 0.1 and 20 mg/kg body weight of the subject to be treated per day, preferably from about 0.2 to 2.5 mg/kg per day, in single or divided doses. If parenteral administration is desired, then it can be given at total daily doses between about 0.1 and 1.0 mg/kg body weight of the subject to be treated. However, at the discretion of the attending physician, some variation in dosage will necessarily occur, depending upon the condition of the subject being treated. The compound is administered alone or in combination with pharmaceutically acceptable carriers or diluents, in either single or multiple doses. Suitable pharmaceutical carriers include inert diluents or fillers, sterile water and various organic solvents. The pharmaceutical compositions formed by combining the N-benzylguanidino compound or salts thereof and pharmaceutically acceptable carriers are readily administered in a variety of dosage forms such as tablets, powders, capsules, lozenges, syrups and the like. These pharmaceutical compositions can, if desired, contain additional ingredients such as flavorings, binders, excipients and the like. Thus, for oral administration, tablets containing various excipients, such as sodium citrate, are employed together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tableting purposes. Solid compositions of a similar type may also be employed as fillers in soft and hard filled gelatin capsules. Preferred materials therefor include lactose or milk sugar and high molecular weight polyethylene glycols. When aqueous suspensions or elixirs are desired for oral administration, the essential active ingredient therein may be combined with various sweetening or flavoring agents, coloring matters or dyes and, if desired, emulsifying agents or suspending agents, together with diluents such as water, ethanol, propylene glycol, glycerin, or combinations thereof. Preferably, the N-benzylguanidino compound is administered orally in unit dosage form, i.e. as a single physically discrete dosage unit containing an appropriate amount of the active compound in combination with a pharmaceutically acceptable carrier or diluent. Examples of such unit dosage forms are tablets or capsules containing from about 5 to 1,000 mg of the active ingredient, the N-benzyl-N'-guanidino or N-pentyl-N'-guanidino compound comprising from about 10% to 90% of the total weight of the dosage unit. For parenteral administration, solutions or suspensions of the compound in sterile aqueous solutions, for example, aqueous propylene glycol, sodium chloride, dextrose or sodium bicarbonate solutions are employed. Such dosage forms are suitably buffered if desired. The preparation of suitable sterile liquid media for parenteral administration will be well known to those skilled in the art.

Most conveniently, the combination of antiinflammatory agents and histamine-$H_2$-antagonists of the present invention are co-administered in a single, combined formulation. This can be in a form suitable for parenteral administration, but is preferably in a form suitable for oral administration. The proportion of each drug in the combined dosage form will be in the ratio of the total daily dosage of each drug when dosed alone, although in some cases the dosage of antiinflammatory drug can be reduced. The combined drugs will be dosed in single or divided doses, generally corresponding to the divided doses of the most frequently dosed drug. For example, according to the Physicians' Desk Reference, 37th Ed., 1983, page 1309, indomethacin is usually administered orally in quantities of 50-200 mg/adult patient/day in 2 to 4 divided doses. Even though an antiulcer drug with which indomethacin is combined according to the present invention could be administered alone in a single daily dosage, the dosage will nevertheless be divided to correspond to the dosage frequency of the indomethacin. In this instance, appropriate unit dosage forms will contain 25-50 mg of indomethacin and about 2-500 mg of one of the present antiulcer compounds [based on their daily oral dose of 0.1–20 mg/kg/day, preferably from about 0.1 to 2.5 mg/kg/day in single or divided doses, as disclosed, for example, in U.S. Pat. Nos. 4,374,843 and 4,435,396 as cited above].

On the other hand, piroxicam, a longer acting antiinflammatory agent, is generally dosed once a day at a level of 20 mg/adult patient/day. When combined with a shorter acting antiulcer compound, dosage will be divided and unit dosages form for 2–4 divided daily doses will contain 5–10 mg of piroxicam and 2–500 mg of the antiulcer compound. However, when combined with a long-acting antiulcer drug such as present 2-guanidino-4-(2-methyl-4-imidazolyl)thiazole or 2-(N-pentyl-N'-guanidino)-4-(2-methyl-4-imidazolyl)-thiazole, dosage will usually be once a day. The more preferred daily dose range for the latter drugs is 3–100 mg/adult patient/day, in combination with 5–50 mg of piroxicam, the dosage of piroxicam lower in the range being possible in the treatment of rheumatoid arthritis as a result of the enhancement of its activity by the antiulcer drug. The most preferred daily dosage range is 12–80 mg of the latter in combination with 10–20 mg of piroxicam.

The combined compounds are administered alone or in further combination with pharmaceutically-acceptable carriers or diluents. For oral dosage, suitable pharmaceutical carriers include inert diluents or fillers, thereby forming dosage forms such as tablets, powders, or capsules. These pharmaceutical compositions can, if desired, contain additional ingredients such as flavorings, binders, excipients and the like. Thus, for oral administration, tablets containing various excipients, such as sodium citrate, are employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tableting purposes. Solid compositions of a similar type may also be employed as fillers in soft and hard filled gelatin capsules. Preferred materials therefor include lactose or milk sugar and high molecular weight polyethylene glycols.

The present invention is illustrated by the following examples. However, it should be understood that the invention is not limited to the specific details of these examples.

EXAMPLE 1

Inhibition of Indomethacin Induced Ulcers by 2-Guanidino-4-(2-methyl-4-imidazolyl)thiazole and 2-Guanidino-4-(2-hexylamino-4-imidazolyl)thiazole Rats for testing were ordered to arrive the week before being tested, and acclimated that first week. Male, CD strain rats were used. By ordering at 100–125 grams, body weights during the second week generally ranged from 150–200 grams. Rats were fasted the day before the test, with food removed from the gang cages no later than 4 p.m. Following an overnight fast a loss of 15–20 grams body weight was anticipated, so volumes of test solutions required for the following day could be estimated. Water was allowed ad lib overnight and during the test itself. On the test day both oral and intraperitoneal dosing was done with volumes of 4.0 ml/kg. Therefore, by knowing approximate body weights (and therefore required volumes) as well as drug doses (mg/kg) to be used, the amount of antiulcer drug and indomethacin needed was determined and preweighed into test tubes the day before the test.

The antiulcer drugs to be tested, in the form of their dihydrochloride salts, were put into solution or suspended. Distilled water was normally the vehicle used. Indomethacin was suspended in saline and homogenized with a small drop of Tween 80 (polysorbate 80) to prevent aggregation of particles. The indomethacin will not stay suspended in the saline, and it is critical that the test tube be well vortexed and the drug resuspended before each dose is drawn into a syringe.

A random sample of the rats to be tested (usually about 20% of the total test group) was used to determine average body weight of the group. Because all dosing was carried out at 4.0 ml/kg, dividing the average weight by 250 g gave the appropriate dosage volume for each rat. The rats were removed from the gang cage, given the test drug or vehicle p.o., and placed in individual cages.

The timing of antiulcer drug dosing relative to the indomethacin challenge varied depending on the specific protocol used. As a typical test consisted of 7 groups of 7 rats each, a predose time of 45 minutes was conveniently used. This allowed about one minute to orally dose each rat. Indomethacin was administered i.p. after the predose time had elapsed. In the typical test mentioned above, this required going back to the first rat and beginning indomethacin injections as soon as the drug dosing was completed. To keep the predose time consistent, rats were also given the indomethacin at a rate of about one per minute.

If the test compound was not expected to have a long duration of action, it was desirable to administer a second dose of antiulcer drug during the test. The typical time between indomethacin administration and sacrifice is 6.5 hours. Adding the 45 minutes predose time to this gives a total time of 7.25 hours, and if a second dose of drug was desired, it was given at the midpoint, or about 3.5 hours after the initial drug dose. Of course, control animals were also dosed with vehicle at this time.

The rats were sacrificed 6.5 hours after administration of the indomethacin. The stomachs were excised, opened along the greater curvature, and rinsed under running water. Lightly rubbing the mucosa while holding it in the stream of water helped to remove some mucus and large clots of blood, but vigorous rubbing was avoided as it may dislodge blood from the indomethacin-induced hemorrhagic erosions, making the erosions extremely difficult to see.

Next the stomachs were placed flat, mucosa side up, on a tray covered with saline-soaked towels. The lesions were then counted, or the stomachs held overnight for examination the following day. If they were stored overnight, the stomachs were first moistened with saline and placed in a polyethylene bag and in a refrigerator.

The indomethacin-induced gastric lesions usually appeared as dark brown or black colored erosions in the corpus (the acid-secreting portion) of the stomach. The dark coloration is caused by the action of the gastric acid on blood within the erosion. Lesions were either punctate or linear in nature. Quantitative determination of lesion size has shown that the average lesion length is about 1 mm. Regardless of size, each individual lesion was counted as one. However, if one group of animals obviously had lesions of a different nature than the controls, this fact was recorded. Some lesions may not have the distinctive dark coloration, but upon close inspection will still be visible as an erosion. Wide variability in the number of lesions in any one group is not uncommon. However, if one result of a group looks suspiciously high or low, the 4d rule is applied as a criterion for the rejection of an observation.

The $ID_{50}$ values, i.e. the dose (mg/kg of free base) necessary to reduce the number of indomethacin-induced gastric lesions in rats to 50% of the number found in controls, were calculated by linear regression analysis (least squares method). Typical results are shown in Table I.

TABLE I

| | Prevention of Indomethacin-Induced Lesions | | | |
|---|---|---|---|---|
| | $ID_{50}$ p.o. (mg/kg) Compound: | | | |
| Dosing Schedule | $A^a$ | $B^b$ | $C^c$ | $D^d$ |
| Single drug dose | 1.4 | — | — | 7.5 |
| Two drug doses | 1.5 | 10.5 | 4.4 | 2.0 |

[a] Compound A is 2-guanidino-4-(2-methyl-4-imidazolyl)thiazole, in the form of its dihydrochloride salt. Since the lowest dose of this compound tested, 2.2 mg/kg, caused a reduction in lesion number that was greater than 50% (63%), the $ID_{50}$'s for this compound were obtained by extrapolation, assuming that a dose of 0.075 mg/kg has no effect.
[b] Compound B is 2-guanidino-4-(2-hexylamino-4-imidazolyl)thiazole, in the form of its dihydrochloride salt.
[c] Compound C is 2-(N—benzylguanidino)-4-(2-methyl-4-imidazolyl)thiazole, in the form of its dihydrochloride salt.
[d] Compound D is 2-guanidino-4-(4-imidazolyl)thiazole in the form of its dihydrochloride salt, made from monohydrobromide according to the method of Examples 5 and 6 below.

EXAMPLE 2

Protective Effect of 2-Guanidino-4-(2-methyl-4-imidazolyl)thiazole on Piroxicam-Induced Gastric Lesions in Rats Adult male "specific pathogen free" rats weighing 140–160 grams of the CD strain (Sprague-Dawley) were obtained from Charles River Breeding Laboratories (Kingston, N.Y.). The animals were acclimated for approximately one week and tested when they reached a body weight of 200–225 grams. The rats were fasted for 16 hours and randomized into groups consisting of 8 to 10 animals which were normalized with regard to their average body weight. Gastric ulcers were induced in the animals by orally dosing the animals with a single 100 mg/kg dose of piroxicam solution containing the drug dissolved in 2 ml 0.1% methylcellulose in water (pH=6.8). Those animals receiving 2-guanidino-4-(2-methyl-4-imidazolyl)thiazole (0.3, 1.0, 3.3 or 10.0 mg/kg as the dihydrochloride salt) separately received that drug, dissolved in an additional 2 ml of the same medium, at about the same time. Six and one-half hours later, the animals were sacrificed by cervical dislocation and autopsied. The stomachs were surgically removed, dissected along the greater curvature and rinsed with cold water. The stomachs were individually scored for both linear and punctate lesions. The total number of lesions was used for scoring purposes. The data obtained from each group of rats was analyzed after calculation of the mean number +/− the standard error of total gastric lesions. The values obtained were also compared to the controls which received only piroxicam by the two-tailed Student's t-test for nonpaired data. The protective effect of 2-guanidino-4-(2-methyl-4-imidazolyl) thiazole against piroxicam-induced ulcers is shown in Table II. These data show 2-guanidino-4-(2-methyl-4-imidazolyl)thiazole significantly reduced piroxicam-induced gastric lesions, showing a dose related response in the range of 0.3–10 mg/kg p.o. From these data was calculated by linear regression analyses, a correlation coefficient (r) of 0.97 and an $ED_{50}$ of 0.32 mg/kg.

TABLE II

| Effect of 2-Guanidino-4-(2-methyl-4-imidazolyl)-thiazole on Piroxicam-induced Gastric Lesions | | |
|---|---|---|
| Oral Dose (mg/kg)*** | Number Rats in Study | Gastric Lesions/Rat X +/− (SE)* |
| 0.0 | 156 | 7.8 (0.4) |
| 0.3 | 26 | 4.1 (0.2)** |
| 1.0 | 156 | 2.6 (0.4)** |
| 3.3 | 86 | 1.3 (0.3)** |
| 10.0 | 56 | 0.8 (0.3)** |

*Mean value +/− standard error; all rats received an ulcerogenic dose (100 mg/kg p.o.) of piroxicam.
**Significantly different (p <<0.05) from rats receiving piroxicam alone as determined by Student's t-test for non-paired data.
***As dihydrochloride salt.

EXAMPLE 3

Protective Effect of 2-Guanidino-4-(2-methyl-4-imidazolyl)thiazole on Gastric Lesions in Rats Induced by the Ethanolamine Salt of Piroxicam According to the preceding Example, gastric ulcers were induced by a single dose of 100 mg of the ethanolamine salt of piroxicam. Test groups received 0.3, 1.0 and 3.3 mg/kg doses of 2-guanidino-4-(2-methyl-4-imidazolyl)thiazole. Results are shown in Table III. These data show that the test compound showed a significant reduction in gastric lesions induced by the ethanolamine salt of piroxicam, showing a dose related response in the range 0.3–3.3 mg/kg. From these data was calculated, by linear regression analyses, a correlation coefficient (r) of 1.00 and an $ED_{50}$ of 0.88 mg/kg.

TABLE III

| Effect of 2-Guanidino-4-(2-methyl-4-imidazolyl)-thiazole on Gastric Lesions Induced by the Ethanolamine Salt of Piroxicam | | |
|---|---|---|
| Oral Dose (mg/kg)*** | Number Rats in Study | Gastric Lesions/Rat X +/− (SE)* |
| 0.0 | 40 | 6.9 (0.7) |
| 0.3 | 40 | 4.2 (0.6)** |
| 1.0 | 40 | 3.4 (0.5)** |
| 3.3 | 40 | 2.4 (0.5)** |

*Mean value +/− standard error (SE); all rats received an ulcerogenic dose (100 mg/kg p.o.) of piroxicam ethanolamine salt.
**Significantly different (p <<0.05) from rats receiving piroxicam ethanolamine salt alone as determined by Student's t-test for non-paired data.
***As dihydrochloride salt.

This test was repeated, using 120 mg of the ethanolamine salt of piroxicam to induce ulcers. The results are shown in Table IIIA. From these data an $ED_{50}$ of 0.3 mg/kg was calculated by linear regression analyses.

TABLE IIIA

| Effect of 2-Guanidino-4-(2-methyl-4-imidazolyl) thiazole on Gastric Lesions Induced by the Ethanolamine Salt of Piroxicam | | |
|---|---|---|
| Oral Dose (mg/kg)*** | Number Rats in Study | Gastric Lesions/Rat X +/− (SE)* |
| 0.0 | 30 | 9.8 (0.9) |
| 0.33 | 30 | 4.7 (0.7)** |
| 1.00 | 30 | 3.1 (0.6)** |
| 3.33 | 30 | 1.7 (0.4)** |

*Mean value +/− standard error (SE); all rats received an ulcerogenic dose (120 mg/kg p.o.) of piroxicam ethanolamine salt.
**Significantly different (p <0.05) from rats receiving piroxicam ethanolamine salt alone as determined by Student's t-test for non-paired data.
***As dihydrochloride salt.

EXAMPLE 4

The Effect of 2-Guanidino 4-(2-methyl-4-imidazolyl)thiazole on the Efficacy of Piroxicam on Adjuvant-Induced Arthritis in the Rat Adjuvant arthritis was induced in adult male Wistar-Lewis rats weighing 250-270 grams each (Charles River Breeding Laboratories, Kingston, N.Y.) by a single subplantar injection of 1 mg of *Mycobacterium butyricum* (Difco Laboratories, Lot #0640-33) suspended in 0.1 ml mineral oil as described by Walz et al. (Proc. Soc. Exptl. Biol. Med., 136: 907-910, 1971). Seven rats were used in each group. Orally administered drugs were dissolved in water and dilute sodium hydroxide was added as necessary to ensure solution; control groups received only water. After neutralization of the solutions to pH 7.0, a volume of 10 ml/kg body weight was given by intubation with a blunt end, 18-gauge needle. Doses of each drug were given daily starting 1 day before the injection of adjuvant and continuing until 16 days after the induction of the arthritic lesion.

The initial hindpaw volumes (Vi) were measured on the day of adjuvant injection and the resultant swelling was determined on the injected paw (Vf - Vi) on the 4th day following the adjuvant injection. This was considered to be the primary response or lesion. The swelling (Vf - Vi) measured 16 days after adjuvant injection on the contralateral, non-injected hindpaw constituted the secondary response or lesion. The rats were weighed at the start of the experiments as well as 4 and 16 days after the induction of the disease. Percent inhibition of edema was calculated according to the following formula:

$$\% \text{ Inhibition of Edema} = \left[1 - \frac{Vf\,\text{drug} - Vi\,\text{drug}}{Vf\,\text{control} - Vi\,\text{control}}\right] \times 100$$

Results are shown in Tables IV and V. As calculated by linear regression analysis, the data in Table IV show that piroxicam alone showed a correlation coefficient (r) of 0.95 and an $ED_{50}$ of 2.60 mg/kg against primary lesions; and r=1.00 and $ED_{50}$=0.45 mg/kg against secondary lesions. For 2-guanidino-4-(2-methyl-4-imidazolyl)thiazole, no significant activity was noted for primary lesions; while significant activity against secondary lesions was noted, no reliable $ED_{50}$ could be extrapolated from this data. The data in Table V indicate that increasing doses of 2-guanidino-4-(2-methyl-4-imidazolyl)thiazole appear to render piroxicam more effective in reducing the swelling observed in the secondary lesion. Thus, the $ED_{50}$ for piroxicam alone shifted from 0.45 mg/kg alone to as low as an $ED_{50}$ of 0.10 mg/kg when dosed in combination with 10 mg/kg of 2-guanidino-4-(2-methyl-4-imidazolyl)thiazole. This shift represents a 5 fold increase in the potency of piroxicam. Similar, but presently less reliable observations were made with regard to the primary lesion.

TABLE IV

The Comparative Effect of Piroxicam and 2-Guanidino-4-(2-methyl-4-imidazolyl)thiazole (Compound A) on Adjuvant-Induced Arthritis

| Oral Dose (mg/kg) | | % Inhibition of Lesions X +/− (SE)* | |
|---|---|---|---|
| Piroxicam | Compound A*** | Primary | Secondary |
| 0.10 | — | 29 (4)** | 26 (2)** |
| 0.33 | — | 33 (8)** | 43 (4)** |
| 1.00 | — | 45 (7)** | 64 (3)** |
| — | 1.0 | 0 (6) | 3 (3) |
| — | 3.3 | 0 (3) | 28 (4)** |
| — | 10.0 | 2 (2) | 27 (3)** |

*Mean value of inhibition of edema +/− standard error; 21 rats were used in each dose of piroxicam (14 as the free enol, 7 as the ethanolamine salt); 7 rats were used for each of the two lower doses of compound A, and 14 rats for the 10 mg/kg dose.
**Significantly different (p <0.05) from non-treated arthritic rats as determined by Student's t-test for non-paired data.
***As the dihydrochloride salt.

TABLE V

The Effect of Graded Doses of 2-Guanidino-4-(2-methyl-4-imidazolyl)thiazole (Compound A) on the Efficacy of the Ethanol Amine Salt of Piroxicam in Adjuvant-Induced Arthritis

| Oral Dose (mg/kg) | | Secondary Lesion | | | |
|---|---|---|---|---|---|
| | | | | $ED_{50}$** | |
| Piroxicam | Compound A*** | X*(%) | r** | (mg/kg) | r'** |
| 0.10 | — | 26 | | | |
| 0.33 | — | 43 | 1.00 | 0.45 | |
| 1.00 | — | 64 | | | |
| 0.10 | 1.0 | 27 | | | |
| 0.33 | 1.0 | 61 | 1.00 | 0.24 | |
| 1.00 | 1.0 | 87 | | | |
| 0.10 | 3.3 | 39 | | | |
| 0.33 | 3.3 | 64 | 1.00 | 0.17 | 1.00 |
| 1.00 | 3.3 | 91 | | | |
| 0.10 | 10.0 | 51 | | | |
| 0.33 | 10.0 | 72 | 1.00 | 0.10 | |
| 1.00 | 10.0 | 93 | | | |

*See corresponding footnote, Table IV.
**Correlation coefficient (r, r') and $ED_{50}$ calculations performed using linear regression analyses; r denotes relationship between piroxicam dose and swelling efficacy and r' denotes the relationship between the dose of Compound A and the observed $ED_{50}$ for inhibition of swelling by piroxicam therapy.
***As the dihydrochloride salt.

EXAMPLE 5

2-Guanidino-4-(2-methyl-4-imidazolyl)thiazole (Free Base)

2-Guanidino-4-(2-methyl-4-imidazolyl)thiazole monohydrobromide (360.7 g, 1.19 mole; U.S. Pat. No. 4,374,843) was slurried in 7500 ml $H_2O$ for 15 minutes at 19° C. With stirring, the pH was slowly adjusted from 5.8 to a stable value of 9.5 with 10% NaOH, 500±5 ml being required. After stirring a further 0.5 hours, title product was recovered by filtration on sintered glass. The sticky cake was washed with 2000 ml $H_2O$, pulled to a tight cake and finally washed with 1000 ml of hexane. After air drying on the funnel for 18 hours, the entire still-partially-wet cake was taken into the next step.

If required for formulation, the free base is dried to constant weight in vacuo, correcting for any remaining water in the formulation.

EXAMPLE 6

2-Guanidino-4-(2-methyl-4-imidazolyl)thiazole Dihydrochloride

The entire batch of partially-wet, free base of the preceding Example, presumed to contain the theoretical 265.3 g of free base on an anhydrous basis, was combined with 1030 ml of CH$_3$OH and 4125 ml of isopropanol and heated to reflux. The hot solution was treated with 62 g activated carbon. After refluxing for 30 minutes, the hot mixture was filtered over diatomaceous earth with 2750 ml of hot isopropanol for wash. The combined filtrate and wash was diluted with an additional 2750 ml of isopropanol, now at 60° C. With stirring, concentrated HCl (345 ml) was added in a thin stream. The resulting suspension was concentrated to 2750 ml in vacuo, chased with 5500 ml of isopropanol while maintaining that volume, cooled to 0°–5° C., stirred 1.5 hours at that temperature, and title product recovered by filtration, washed with 700 ml cold isopropanol and dried in vacuo at ambient temperature; 307.2 g (87%) over two steps, m/e 222; u.v. lambda max. (0.01N HCl/CH$_3$OH) 229 and 260 nm (E$_{1cm}$$^{1\%}$ 661 and 569); lambda max. (0.01N NaOH/CH$_3$OH) 248 and 274 nm (E$_{1cm}$$^{1\%}$ 681 and 475); neutralization equivalent (1:1 ethanol:H$_2$O with 0.5N NaOH) calcd. 295.2; found 299.9.

Analysis calculated for C$_8$H$_{10}$N$_6$S.2HCl: C, 32.55; H, 4.10; N, 28.47; S, 10.86; Cl$^-$, 24.02%. Found: C, 32.30; H, 4.06; N, 28.29; S, 11.05; Cl$^-$, 24.05%.

Alternatively, free base (10.0 g, 0.045 mol, weight corrected for up to 20% water content) was dissolved in 100 ml of hot glacial acetic acid, an amount just sufficient for complete dissolution at near reflux temperature. The hot solution was diluted with 10 ml additional hot acetic acid and then 7.5 ml (0.090 mol) of concentrated HCl was added. Title product, which began to crystallize almost immediately, was recovered by filtration after cooling to room temperature, and dried in vacuo at 40° C.; yield 12.63 g (95%), identical with the product crystallized from isopropanol.

Alternatively, free base (1.0 g, 0.0045 mol) was dissolved in 2 ml concentrated HCl. The dihydrochloride crystallized almost immediately. The mixture was diluted with 5 ml acetone, stirred 5 minutes, and title product recovered by filtration with acetone wash, 1.15 g (86.6%), identical with the product of Method A above.

Analysis calculated for C$_8$H$_{10}$N$_6$S.2HCl: C, 32.55; H, 4.10; N, 28.47%. Found: C, 32.16; H, 4.40; N, 28.09%.

EXAMPLE 7

2-Guanidino-4-(2-methyl-4-imidazolyl)thiazole Dihydrobromide

Method A

2-Methyl-4-acetylimidazole (4.00 g, 0.0322 mol; U.S. Pat. No. 4,374,843) was dissolved in 48% HBr (40 ml, 0.351 mol), the temperature rising to 33° C. The solution was heated to 50° C. Br$_2$ (1.65 ml, 5.15 g, 0.0322 mol) in 5 ml of 48% HBr was added dropwise over 17 minutes maintaining that temperature with external heating as necessary. The stirred reaction mixture was heated to 65° C. for 1.5 hours, cooled and stripped to a cream-colored slurry. The mixture was chased 2×20 ml H$_2$O (the solids dissolving and returning to a thick slurry each time). Without further isolation of the intermediate 2-methyl-4-(bromoacetyl)imidazole, absolute ethanol (29.2 ml) was added, and then N-amidinothiourea (3.81 g, 0.0322 mol) and the slurry heated to reflux. The resulting solution was refluxed for 2 hours, by which time there was heavy precipitation of crystalline title product. The slurry was distilled to half-volume, cooled to room temperature, and title product recovered by filtration with a small amount of ethanol wash and dried at 35° C. in vacuo; 10.12 g (79% over two chemical steps); homogeneous by tlc Rf 0.75 (19:1 ethanol:concentrated NH$_4$OH); m.p. 300° C. (decomposition).

Analysis calculated for C$_8$H$_{10}$N$_6$S.2HBr.0.5H$_2$O: C, 24.44; H, 3.33; N, 21.38%. Found: C, 24.20; H, 3.18; N, 21.43%.

Method B

In the manner of Method A, 2-methyl-4-acetylimidazole (4.00 g, 0.0322 mol) was brominated, but with substitution of 3.67 ml (0.0322 mol) of 48% HBr and 4 ml of acetic acid for the initial charge of 48% HBr, and charging the Br$_2$ (1.65 ml) in 4 ml of acetic acid in place of 48% HBr. At the end of the 1.5 hour heating period (*without* cooling, stripping and chasing), the N-amidinothiourea (3.81 g) was added. The reaction exothermed from 67 to 77° C., and the resulting solution was heated at 80° C. for 1 hour during which title product began to precipitate heavily. Title product was recovered as in Method A, 9.34 g (73% over two chemical steps), identical with the product of Method A.

Method C

To 48% HBr (16.9 ml) was added 2-methyl-4-acetylimidazole (7.36 g, 0.059 mol) to form a clear yellow solution. Br$_2$ (3.0 ml, 0.059 mol) in 48% HBr (3.3 ml) was added dropwise as the reaction was warmed to 45° C. Transient precipitation was noted during addition and heating. After stirring for 18 hours at 45° C., the reaction mixture was cooled to 30° C., diluted with 22 ml absolute ethanol, and N-amidinothiourea (7.0 g) was added. The resulting slurry almost became clear, then set up to solids which were broken up with a spatula. The resulting mobile slurry was stirred at 55° C. for 2 hours, cooled to 10° C., and title product recovered by filtration with 2×5 ml absolute ethanol wash, 20.3 g (86%), identical with title product of Method A.

EXAMPLE 8

2-Guanidino-4-(2-methyl-4-imidazolyl)thiazole (Free Base)

2-Guanidino-4-(2-methyl-4-imidazolyl)thiazole dihydrobromide (13.4 g) was stirred with 66.9 ml H$_2$O and the pH slowly adjusted to a stable value of 10.0 over 2 hours with 22.6 ml of 3N NaOH while maintaining a temperature of 22°–24° C. Title product was recovered by suction filtration with water wash, pulled to a tight cake under a rubber dam, repulped in 28 ml acetone for 2 hours, refiltered, washed with 12 ml acetone and dried at 40° C. in vacuum to yield crystalline title product, 8.66 g, containing about 15% water.

Anhydrous free base was prepared from water-wet cake (prepared as above, without acetone repulp) by dissolving 4.04 g of the water-wet cake (estimated to contain 1.60 g of free base on a dry basis) in 80 ml of refluxing acetone, treating the solution with 0.16 g activated carbon, filtering hot, concentrating the filtrate to 15 ml, stirring at room temperature for 1 hour, filtering with acetone wash and drying the cake at 40° C. in vacuo; yield: 1.57 g.

EXAMPLE 9

2-(N-Benzyl-N'-guanidino)-4-(2-methyl-4-imidazolyl)-thiazole Dihydrochloride

To a solution of 13.08 g (46.05 mmole) 2-bromo-1-(2-methylimidazol-4-yl)ethanone hydrobromide in 150 ml acetone was added a solution of 10.53 g (50.66 mmole) 1-(N-benzylguanyl)thiourea in 50 ml acetone, the mixture refluxed for six hours and allowed to stand at room temperature for 16 hours. The mixture was heated at reflux for an additional hour, cooled and the crude product collected as its dihydrobromide salt. This was dissolved in 300 ml water and added to a solution of 20.59 g (166 mmole) sodium carbonate monohydrate in 200 ml water. After standing for 15 minutes the solid was filtered and washed with water. The damp solid was dissolved in 400 ml acetone, filtered to remove insoluble material, and the filtrate treated with 8 ml 37% (w/v) concentrated hydrochloric acid. The acidified mixture was stirred for 1.5 hours, filtered and the collected solid dried to yield a light yellow solid. This was dissolved in 50 ml methanol, carbon treated and filtered through diatomaceous earth. The filtrate was diluted with isopropyl ether and the solid precipitate collected by filtration and dried to afford 14.36 g (81%) of the title product; m.p. 306°–307° C.; m/e 312. Analysis calculated for $C_{15}H_{16}N_6S \cdot 2HCl$: C, 46.75; H, 4.71; N, 21.81; Cl, 18.40. Found: C, 46.48; H, 4.82; N, 21.94; Cl, 18.04.

The dihydrobromide salt was prepared in like manner by substituting 48% hydrobromic acid in place of hydrochloric acid.

EXAMPLE 10

4-(2-Methyl-4-imidazolyl)-2-(N-pentyl-N'-guanidino)-thiazole Dihydrochloride (N-Pentylguanyl)thiourea (21.12 g, 0.112 mol) and 4-bromoacetyl-2-methylimidazole hydrobromide (27.65 g, 0.097 mol) were combined in acetone (400 ml) and refluxed for 24 hours. The resulting solid was collected, washed with acetone and dried yielding 40.63 g (92.2%) of light yellow dihydrobromide salt of the desired product.

Dihydrobromide salt (81.14 g, 0.179 mol) was dissolved in warm water (1500 ml) and added slowly to a solution of sodium carbonate monohydrate (88.6 g, 0.714 mole) in water (800 ml). After complete addition the mixture was stirred for 30 minutes and was then filtered. The filter cake was washed thoroughly with water and dried in vacuo for 48 hours. This solid was dissolved in acetone (2 l), filtered to remove small amounts of suspended material, acidified with conc. HCl (34 ml, 0.408 mole) and diluted with additional acetone (1 l). The resulting precipiate was collected, washed and dried yielding 62.44 g (93.2%) of off-white solid; mp 299°–301°.

Anal. Calcd. for $C_{13}H_{20}N_6S \cdot 2HCl \cdot 0.5H_2O$: C, 41.71; H, 6.19; N, 22.45; $Cl^-$, 19.41. Found: C, 41.75; H, 6.21; N, 22.42; $Cl^-$, 19.03.

EXAMPLE 11

Histamine-$H_2$ Antagonist Activity

The histamine-$H_2$ antagonist activity of the product of the two preceding Examples was determined by the following procedure:

Guinea pigs are killed rapidly with a blow to the head, the heart removed and the right atria dissected free. Atria are suspended, isometrically, in a temperature-controlled (32°±2° C.) tissue bath (10 ml) containing oxygenated (95% $O_2$; 5% $CO_2$) Krebs-Henseleit buffer (pH 7.4) and are allowed to stabilize approximately one hour during which time the tissue bath is flushed several times. Individual atrial contractions are followed with a force-displacement transducer connected to a cardiotachometer and Grass polygraph recorder. After obtaining a dose-response curve to histamine, the bath containing each atrium is flushed several times with fresh buffer and the atria reequilibrated to basal rates. Following the return to basal rate, test compounds are added at selected final concentrations and the histamine dose-response curve is again determined in the presence of antagonist. Results are expressed as dose-ratios, the ratio of histamine concentrations required to produce one-half of maximal stimulation in the presence and absence of antagonist, and the apparent dissociation constant of the $H_2$-receptor antagonist $pA_2$, is determined.

The compound of the preceding two Examples, tested as the dihydrobromide salts, gave a $pA_2$ value of at least 7.2.

EXAMPLE 12

Inhibition of Ethanol-Induced Ulceration in Rats

The antiulcer activity of the products of Examples 9 and 10 was also determined by an ethanol-induced rat ulcer assay. In this test, overnight fasted male rats are given drug (at 30 or 3 mg/kg) or water orally fifteen minutes prior to an orally administered dose of absolute ethanol (1.0 ml). One hour after the ethanol challenge the animals (8/group) are killed and the stomachs examined for the presence of lesions. After sacrifice the abdomen is opened and a locking hemostat placed at the pylorus. Six ml of a 4% solution of formaldehyde was injected into the stomach with a gastric feeding tube and a second locking hemostat was used to seal the esophagus. The stomach was removed, opened along the greater curvature and examined for ulceration.

The scoring system used to quantitate the ethanol-induced lesions is given below.

| Ulcer Score Table | |
|---|---|
| Score | Definition |
| 1 | Normal appearing stomach |
| 2 | Pinpoint sized lesions |
| 3 | Lesions, 2 or fewer; pinpoint lesions may be present |
| 4 | Lesions, >2; pinpoint lesions may be present |
| 5 | Lesions with hemorrhage |

For each group of animals an ulcer index is calculated as follows:

Ulceration Index = (the sum of the scores of the group) ×

(the sum of the number of ulcers in the group) ×

(the fraction of the group having any incidence of ulceration).

The percentage inhibition of ulcers is calculated as follows:

% Inhibition = 100 × [(ulcer index controls) −

(ulcer index drug-treated)] ÷ (ulcer index controls).

At an oral dose of 30 mg/kg, the compound of Examples 9 and 10, tested as the dihydrobromide salts showed at least 77% inhibition of ethanol-induced ulceration. At an oral dose of 3 mg/kg these compounds showed at least 40% inhibition of ulceration.

EXAMPLE 13

Protective Effect of
2-(N-Pentyl-N'-Guanidino)-4-(2-methyl-4-imidazolyl)-
thiazole on Gastric Lesions in Rats Induced by the
Ethanolamine Salt of Piroxicam According to Examples 2 and 3, gastric ulcers were induced by a single dose of 120 mg of the ethanolamine salt of piroxicam. Test groups received 0.03, 0.10 and 0.33 mg/kg doses of 2-(N-pentyl-N'-guanidino)-4-(2-methyl-4-imidazolyl)thiazole dihydrochloride. Results are shown in Table VI. These data show that the test compound showed a significant reduction in gastric lesions induced by the ethanolamine salt of piroxicam, showing a dose related response in the range 0.03–0.33 mg/kg. From these data was calculated, by linear regression analyses, an $ED_{50}$ of 0.1 mg/kg.

TABLE VI

Effect of 2-(N—Pentyl-N'—guanidino-4-(2-methyl-4-imidazolyl)thiazole on Gastric Lesions Induced by the Ethanolamine Salt of Piroxicam

| Oral Dose (mg/kg)*** | Number Rats in Study | Gastric Lesions/Rat X +/− (SE)* |
|---|---|---|
| 0.0 | 30 | 9.8 (0.9) |
| 0.03 | 30 | 6.6 (1.0) |
| 0.10 | 30 | 3.4 (1.0)** |
| 0.33 | 29 | 2.4 (0.9)** |

*Mean value +/− standard error (SE); all rats received an ulcerogenic dose (100 mg/kg p.o.) of piroxicam ethanolamine salt.
**Significantly different (p <0.05) from rats receiving piroxicam ethanolamine salt alone as determined by Student's t-test for non-paired data.
***As dihydrochloride salt.

EXAMPLE 14

Capsules - Piroxicam (20 mg) and
2-Guanidino-4-(2-methyl-4-imidazolyl)thiazole (20 mg)

The following ingredients are combined in the following proportions by weight:

| | |
|---|---|
| piroxicam (milled) | 20 |
| 2-guanidino-4-(2-methyl-4-imidazolyl)thiazole dihydrochloride (milled) | 26.6* |
| calcium carbonate | 45 |
| polyethylene glycol, average molecular weight, 4000 | 158.4 |

*equivalent to 20 parts of free base

The mixture is thoroughly blended so as to obtain a uniform powder. Soft gelatin capsules containing 20 mg of each active component are then prepared by filling suitably sized capsules with 250 mg of the blend.

To make hard gelatin filled capsules, the amount of inert ingredients is adjusted so as to conveniently fill standard sized gelatin capsules containing 20 mg of each active component.

EXAMPLE 15

Capsules - Piroxicam (20 mg) and
2-Guanidino-4-(2-methyl-4-imidazolyl)thiazole (50 mg)

The following ingredients are combined in the following proportions by weight:

| | |
|---|---|
| piroxicam ethanolamine salt (milled) | 23.7* |
| 2-guanidino-4-(2-methyl-4-imidazolyl)thiazole (milled) | 50 |
| corn starch | 623.3 |
| magnesium stearate | 3 |

*equivalent to 20 parts of free enolic form

The mixture is thoroughly blended so as to form a uniform powder. The resultant mix is filled into size 0 hard gelatin capsules (fill weight 700 mg) so as to obtain capsules containing the desired potency of each active ingredient.

EXAMPLE 16

Capsules - Indomethacin (25 mg) and
2-Guanidino-4-(2-methyl-4-imidazolyl)thiazole (15 mg)

The following ingredients are combined in the following proportions by weight:

| | |
|---|---|
| indomethacin (milled) | 25 |
| 2-guanidino-4-(2-methyl-4-imidazolyl)thiazole (milled) | 15 |
| calcium carbonate | 200 |
| polyethylene glycol, average molecular weight, 4000 | 600 |

The mixture is thoroughly blended so as to obtain a uniform powder. The resultant mix (840 mg fill weight) is filled into hard gelatin capsules of a suitable size so as to obtain capsules of the desired potency.

EXAMPLE 17

Capsules - Piroxicam (10 mg) and
2-Guanidino-4-(2-hexylamino-4-imidazolyl)thiazole (50 mg)

The following ingredients are combined in the following proportions by weight:

| | |
|---|---|
| piroxicam (milled) | 10 |
| 2-guanidino-4-(2-hexylamino-4-imidazolyl)thiazole dihydrochloride monohydrate (milled) | 64.5* |
| corn starch | 622.5 |
| magnesium stearate | 3 |

*equivalent to 50 parts of free base

The mixture is thoroughly blended to form a uniform powder which is filled into size 0 hard gelatin capsules (fill weight 700 mg) to obtain capsules containing the desired potency of each ingredient.

EXAMPLE 18

Tablets - Piroxicam (20 mg) and
2-Guanidino-4-(2-methyl-4-imidazolyl)thiazole (70 mg)

The following ingredients are combined in the following proportions by weight:

| | |
|---|---|
| piroxicam (milled) | 20 |
| 2-guanidino-4-(2-methyl-4-imidazolyl)thiazole (milled) | 70 |
| lactose | 188 |
| hydroxypropyl methylcellulose | 3 |
| sodium starch glycollate | 15 |
| magnesium stearate | 4 |

The mixture is thoroughly blended to form a uniform powder. Measured volumes of the powder, corresponding to 300 mg by weight, are compressed into tablets containing the desired potency of each active ingredient.

EXAMPLE 19

Tablets - Indomethacin (25 mg) and 2-Guanidino-4-(2-hexylamino-4-imidazolyl)thiazole (25 mg)

The following ingredients are combined in the following proportions by weight:

| | |
|---|---|
| indomethacin (milled) | 25 |
| 2-guanidino-4-(2-hexylamino-4-imidazolyl)thiazole dihydrochloride monohydrate | 32.25* |
| lactose | 217.5 |
| hydroxypropyl methylcellulose | 4 |
| sodium starch glycollate | 16 |
| magnesium stearate | 5 |

*equivalent to 25 parts of free base

The mixture is thoroughly blended to form a uniform powder. The powder, in measured volumes corresponding to 300 mg by weight, is compressed into tablets containing the desired potency of each active ingredient.

EXAMPLE 20

Capsules - Piroxicam (20 mg) and 2-(N-Benzyl-N'-guanidino)-4-(2-methyl-4-imidazolyl)thiazole (20 mg)

The following ingredients are combined in the following proportions by weight:

| | |
|---|---|
| piroxicam (milled) | 20 |
| 2-(N—benzyl-N'—guanidino)-4-(2-methyl-4-imidazolyl)thiazole dihydrochloride (milled) | 24.7* |
| calcium carbonate | 45 |
| polyethylene glycol, average molecular weight, 4000 | 160.3 |

*equivalent to 20 parts of free base.

The mixture is thoroughly blended so as to obtain a uniform powder. The resultant mix is filled into hard gelatin capsules (fill weight 250 mg) to obtain capsules containing 20 mg activity of each active ingredient.

EXAMPLE 21

Capsules - Piroxicam (20 mg) and 2-(N-Pentyl-N'-guanidino)-4-(2-methyl-4-imidazolyl)thiazole (20 mg)

The following ingredients are combined in the following proportions by weight:

| | |
|---|---|
| piroxicam (milled) | 20 |
| 2-(N—pentyl-N'—guanidino)-4-(2-methyl-4-imidazolyl)thiazole dihydrochloride (milled) | 25.0* |
| corn starch | 602 |
| magnesium stearate | 3 |

*equivalent to 20 parts of free base.

The mixture is thoroughly blended so as to form a uniform powder. The resultant mix is filled into hard gelatin capsules of appropriate size (fill weight 650 mg) so as to obtain capsules containing the desired potency of each active ingredient.

EXAMPLE 22

Tablets - Piroxicam (10 mg) and 2-(N-Pentyl-N'-guanidino)-4-(2-methyl-4-imidazolyl)thiazole (20 mg)

The following ingredients are combined in the following proportions by weight:

| | |
|---|---|
| piroxicam | 10 |
| 2-(N—pentyl-N'—guanidino)-4-(2-methyl-4-imidazolyl)thiazole dihydrochloride | 25* |
| lactose | 193 |
| hydroxypropyl methylcellulose | 3 |
| sodium starch glycolate | 15 |
| magnesium stearate | 4 |

*equivalent to 20 parts of free base

The mixture is thoroughly blended to form a uniform powder. Measure volumes, corresponding to 250 mg by weight, are compressed into tablets containing the desired potency of each active ingredient.

PREPARATION 1

N-Pentyl-N'-cyanoguanidine

Pentylamine (17.43 g, 0.20 mol) in 2-propanol (175 ml) was acidified with conc. HCl (17 ml, 0.204 mol) and then treated with sodium dicyanamide (23.15 g, 0.26 mol). The mixture was refluxed for 20 hours, allowed to cool and filtered through Celite. The filtrate was concentrated in vacuo and the residue dissolved in chloroform. This solution was washed with water and dried over magnesium sulfate. Filtration and evaporation in vacuo gave 20.93 g (67.9%) of off-white solid; mass spec.: M+ at 154.

PREPARATION 2

(N-Pentylguanyl)thiourea

N-Pentyl-N'-cyanoguanidine (30.0 g, 0.195 mol) and diethylamine (3 ml) were combined in methanol (550 ml). This solution was cooled to −40°, saturated with hydrogen sulfide gas, transferred to a stainless steel bomb and heated at 85° for 40 hours. The excess hydrogen sulfide was purged from the reaction mixture with nitrogen and the solution was then concentrated in vacuo. The residue was flash chromatographed (140 mm column, 5% methanol in chloroform). The fractions containing pure product were combined and evaporated yielding 22.01 g (59.9%) of white solid. A portion was recrystallized from chloroform to furnish material with mp 98°–100°, mass spec.: M+ 188.

PREPARATION 3

N-Benzyl-N'-cyanoguanidine

By the method of Preparation 1, benzylamine was converted to title product, mass spec.: M+ at 175.

PREPARATION 4

To a solution of 6.73 g (38.6 mmols) 1-benzyl-3-cyanoguanidine in 100 ml. methanol is added 2 ml diethylamine, the mixture cooled to 0° C. and saturated with hydrogen sulfide gas. The cold solution was transferred to a stainless steel bomb, sealed and the bomb heated at 80° C. for 48 hours. The mixture was then transferred to a flask, flushed with nitrogen to expel the excess hydrogen sulfide and the solvent evaporated in vacuo. The resulting residual oil was purified by flash chromatography (silica gel) eluting with 20:1 chloroform/methanol to obtain 3.06 g of product as a light yellow oil. Mass spectrum (m/e): 209 (M+).

I claim:

1. A method for the oral treatment of inflammation in man which comprises, in addition to treatment with an antiinflammatory amount of an oxicam having the formula

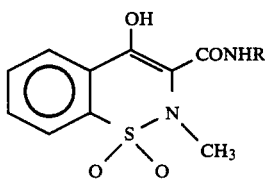

or

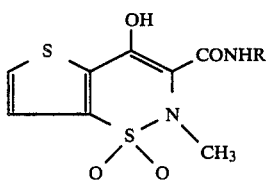

wherein R is

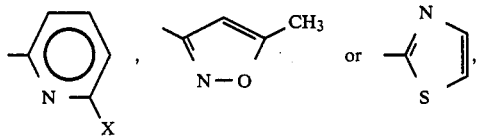

and X is hydrogen, chloro or methyl; or a pharmaceutically acceptable salt thereof; treatment with a gastric anti-irritation and ulcer-inhibiting amount of a compound selected from the group consisting of:
2-guanidino-4-(4-imidazolyl)thiazole;
2-guanidino-4-(2-methyl-4-imidazolyl)thiazole;
2-(N-benzyl-N'-guanidino)-4-(2-methyl-4-imidazolyl)thiazole;
2-(N-pentyl-N'-guanidino)-4-(2-methyl-4-imidazolyl)thiazole;
2-guanidino-4-[2-(hexylamino)-4-imidazolyl]thiazole; and the pharmaceutically acceptable salts thereof.

2. A method of claim 1 wherein the oxicam is tenoxicam, isoxicam or sudoxicam.

3. A method of claim 2 wherein the compound is 2-guanidino-4-(2-methyl-4-imidazolyl)thiazole.

4. A method for the treatment of inflammation which comprises, in addition to treatment with an antiinflammatory amount of piroxicam or a pharmaceutically acceptable salt thereof, treatment with a gastric anti-irritation and ulcer-inhibiting amount of a compound selected from the group consisting of:
2-guanidino-4-(4-imidazolyl)thiazole;
2-guanidino-4-(2-methyl-4-imidazolyl)thiazole;
2-(N-benzyl-N'-guanidino)-4-(2-methyl-4-imidazolyl)thiazole;
2-(N-pentyl-N'-guanidino)-4-(2-methyl-4-imidazolyl)thiazole;
2-guanidino-4-[2-(hexylamino)-4-imidazolyl]thiazole; and the pharmaceutically acceptable salts thereof.

5. A method of claim 4 wherein the piroxicam is in the form of its free acid.

6. The method of claim 5 wherein the compound is 2-guanidino-4-(2-methyl-4-imidazolyl)thiazole in the form of its dihydrorchloride salt.

7. The method of claim 5 wherein the compound is 2-guanidino-4-[2-(hexylamino)-4-imidazolyl]thiazole in the form of its dihydrochloride salt.

8. The method of claim 5 wherein the compound is 2-(N-pentyl-N'-guanidino)-4-(2-methyl-4-imidazolyl)thiazole in the form of its dihydrochloride salt.

9. A method of claim 4 wherein the piroxicam is in the form of its ethanolamine salt.

10. The method of claim 9 wherein the compound is 2-guanidino-4-(2-methyl-4-imidazolyl)thiazole in the form of its free base.

11. An antiinflammatory composition for oral use in man which comprises:

(a) an antiinflammatory amount of an oxicam having the formula

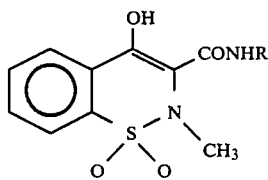

or

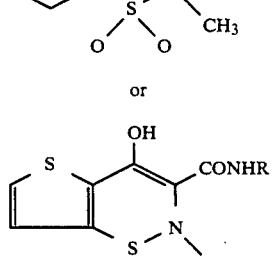

wherein R is

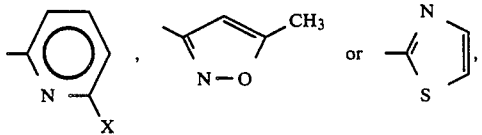

and X is hydrogen, chloro or methyl, or a pharmaceutically acceptable salt thereof; and (b) a gastric anti-irritation and ulcer-inhibiting amount of a compound selected from the group consisting of:
2-guanidino-4-(4-imidazolyl)thiazole;
2-guanidino-4-(2-methyl-4-imidazolyl)thiazole;
2-(N-benzyl-N'-guanidino)-4-(2-methyl-4-imidazolyl)thiazole;
2-(N-pentyl-N'-guanidino)-4-(2-methyl-4-imidazolyl)thiazole;
2-guanidino-4-[2-(hexylamino)-4-imidazolyl]thiazole; and the pharmaceutically acceptable salts thereof.

12. A composition of claim 11 wherein the oxicam is tenoxicam, isoxicam or sudoxicam.

13. A composition of claim 12 wherein the ulcer-inhibiting compound is 2-guanidino-4-(2-methyl-4-imidazolyl)thiazole.

14. An antiinflammatory composition which comprises:

(a) an antiinflammatory amount of piroxicam, or a pharmaceutically acceptable salt thereof;

(b) a gastric anti-irritation and ulcer-inhibiting amount of a compound selected from the group consisting of:
2-guanidino-4-(4-imidazolyl)thiazole;
2-guanidino-4-(2-methyl-4-imidazolyl)thiazole;
2-(N-benzyl-N'-guanidino)-4-(2-methyl-4-imidazolyl)thiazole;
2-(N-pentyl-N'-guanidino)-4-(2-methyl-4-imidazolyl)thiazole;
2-guanidino-4-[2-(hexylamino)-4-imidazolyl]-thiazole; and the pharmaceutically acceptable salts thereof.

15. A composition of claim 14 wherein the piroxicam is in the form of its free acid.

16. The composition of claim 15 wherein the compound is 2-guanidino-4-(2-methyl-4-imidazolyl)thiazole in the form of its dihydrochloride salt.

17. The composition of claim 15 wherein the compound is 2-guanidino-4-[2-(hexylamino)-4-imidazolyl]-thiazole in the form of its dihydrochloride salt.

18. The composition of claim 15 wherein the compound is 2-(N-pentyl-N'-guanidino)-4-(2-methyl-4-imidazolyl)thiazole in the form of its dihydrochloride salt.

19. A composition of claim 15 wherein the piroxicam is in the form of its ethanolamine salt.

20. The composition of claim 19 wherein the compound is 2-guanidino-4-(2-methyl-4-imidazolyl)thiazole in its free base form.

* * * * *